(12) United States Patent
Bly et al.

(10) Patent No.: US 8,554,336 B2
(45) Date of Patent: Oct. 8, 2013

(54) MEDICAL LEAD HAVING A VARIABLE CHANGE IN STIFFNESS

(75) Inventors: Mark J. Bly, Falcon Heights, MN (US);
Brian D. Soltis, St. Paul, MN (US);
Bruce A. Tockman, Scandia, MN (US);
Avram Scheiner, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 723 days.

(21) Appl. No.: 11/277,333

(22) Filed: Mar. 23, 2006

(65) Prior Publication Data
US 2007/0225784 A1    Sep. 27, 2007

(51) Int. Cl.
*A61N 1/00* (2006.01)

(52) U.S. Cl.
USPC ........................................................ 607/116

(58) Field of Classification Search
USPC ................. 607/137, 138, 115–131, 133–135, 607/147–149; 128/899; 600/101; 604/164.01, 604/93.01, 525, 528, 532; 254/134.3
See application file for complete search history.

(56) References Cited

U.S. PATENT DOCUMENTS

| | | | |
|---|---|---|---|
| 4,991,602 A * | 2/1991 | Amplatz et al. | 600/585 |
| 5,423,772 A * | 6/1995 | Lurie et al. | 604/525 |
| 5,441,489 A * | 8/1995 | Utsumi et al. | 604/525 |
| 6,007,478 A * | 12/1999 | Siess et al. | 600/16 |
| 6,188,931 B1 | 2/2001 | Holmstrom et al. | |
| 6,278,897 B1 | 8/2001 | Rutten et al. | |
| 6,390,993 B1 | 5/2002 | Cornish et al. | |
| 6,488,637 B1 * | 12/2002 | Eder et al. | 600/585 |
| 6,556,873 B1 | 4/2003 | Smits | |
| 6,666,829 B2 | 12/2003 | Cornish et al. | |
| 6,718,211 B2 | 4/2004 | Smits | |
| 6,741,893 B2 | 5/2004 | Smits | |
| 6,973,351 B2 | 12/2005 | Morgan | |
| 7,272,449 B2 * | 9/2007 | Dadd et al. | 607/137 |
| 2003/0009095 A1 * | 1/2003 | Skarda | 600/374 |
| 2006/0009829 A1 | 1/2006 | Aron et al. | |

* cited by examiner

*Primary Examiner* — Eric D. Bertram
*Assistant Examiner* — Elizabeth K So
(74) *Attorney, Agent, or Firm* — Faegre Baker Daniels LLP (57) ABSTRACT

According to one embodiment, the present invention includes an elongate implantable medical lead having a distal portion that is relatively flexible, a proximal portion that is relatively stiff, and a transition portion which has a variable transition stiffness. The transition stiffness varies over the length of the transition portion that generally decreases in a distal direction. The relatively stiff proximal portion of the lead gives the lead steerability while the gradual change in stiffness in the transition portion reduces the likelihood that the lead will prolapse when it is guided into a branch vein. The distal stiffness is less than the proximal stiffness giving the lead a safe end that is unlikely to puncture vascular walls and is able to maneuver around various tortuosities when the lead is implanted into a patient.

8 Claims, 11 Drawing Sheets

MEDICAL LEAD HAVING A VARIABLE CHANGE IN STIFFNESS

TECHNICAL FIELD

The present invention relates to medical devices and methods for accessing an anatomical space of the body. More specifically, the invention relates to an elongate implantable medical lead and methods of manufacturing the medical lead.

BACKGROUND

Implantable medical leads are devices that couple electrical pulse generators to cardiac muscle. They are commonly used for delivering an electrical pulse to the cardiac muscle, for sensing electrical signals produced in the cardiac muscle, or for both delivering and sensing. Many complex medical devices utilize implantable leads. Pacemaker systems are used to treat bradycardia (i.e., abnormally slow heart rate) and other heart arrhythmias. Typical pacemaker systems include an implantable pulse generator and one or more leads which form the electrical connection between the implantable pulse generator and the heart. Implantable cardioverter defibrillators ("ICDs") are used to treat tachycardia (i.e., abnormally rapid heart rate). An ICD also includes a pulse generator and one or more leads to deliver electrical energy to the heart.

Implantable leads typically include a flexible conductor surrounded by an insulating tube or shaft that extends from an electrode at the distal end to an electrode at the proximal end. Some known leads include a relatively flexible distal end with a relatively stiff proximal end. The stiffer proximal end allows the lead to be pushed and rotated through the vascular system while the flexible distal end allows the lead to maneuver around physical obstructions, tortuosities and take-off angles. The shift from the stiff proximal end to the flexible distal end is often abrupt. This abrupt shift from a stiff portion to a flexible portion often results in the lead prolapsing, or folding, when the lead is guided into a branch vein, such as a coronary branch vein. Thus, there is a need in the art for a medical lead that gradually transitions from a stiff proximal section to a flexible distal section.

SUMMARY

The present invention according to one embodiment is directed to an elongate implantable medical lead that includes distal portion having a distal stiffness, a proximal portion having a proximal stiffness that is greater than the distal stiffness, and a transition portion located between the proximal portion and the distal portion and having a transition stiffness that decreases in the distal direction.

In another embodiment, the invention is directed toward an elongate implantable medical device that includes an implantable medical lead having a lead stiffness. The device also includes a stylet having a stylet stiffness that decreases in a distal direction. The medical device also includes a composite stiffness that is formed of the stylet stiffness and the lead stiffness and decreases in the distal direction.

In still another embodiment, an elongate implantable medical lead may be manufactured by forming a first mating surface that tapers in a proximal direction with a first polymeric material having a first stiffness, forming a second mating surface that tapers in the proximal direction with a second polymeric material having a second stiffness that is greater that the first stiffness, and mating the first mating surface to the second mating surface.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

According to one embodiment, the present invention includes an elongate implantable medical lead having a distal portion that is relatively flexible, a proximal portion that is relatively stiff, and a transition portion which has a variable transition stiffness. The transition stiffness varies over the length of the transition portion that generally decreases in a distal direction. The relatively stiff proximal portion of the lead gives the lead steerability while the gradual change in stiffness in the transition portion reduces the likelihood that the lead will prolapse when it is guided into a branch vein. The distal stiffness is less than the proximal stiffness giving the lead a safe end that is unlikely to puncture vascular walls and is able to maneuver around various tortuosities when the lead is implanted into a patient.

A variable stiffness may be imparted to the transition portion in any suitable manner. For example, in one embodiment, the transition portion may include different polymeric materials that have various stiffnesses. Suitable polymeric materials that may be used to form the transition portion include polyurethane, silicone, ethylene tetrafluoroethylene (ETFE), polytetrafluoroethylene (PTFE), expanded polytetrafluoroethylene (EPTFE), polycin vorite, and silicone medical adhesive. The thicknesses or concentrations of the polymeric materials may also be varied to create a linear or non-linear change in stiffness in the transition portion.

The shape and number of conductors may also impart a variable stiffness to the lead. The conductors are typically formed of metallic materials such as MP35N (a nonmagnetic, nickel-cobalt-chromium-molybdenum alloy), Tantalum (Ta), Platinum (Pt), Iridium (Ir), or stainless steel. The conductors may be coiled or uncoiled to impart a varying stiffness to the transition portion. The stiffness of the transition portion may also depend on how tightly the coil is wound.

The stiffness of the various portions of the lead according to the present invention may be measured using any standard method. One method includes measuring the force required to bend or deflect a 10 mm section of the lead a distance of 0.5 mm. In this method, a section of the lead is cut to a distance of over 10 mm, such as, for example, 15 mm. The lead 15 mm section may then be secured at two points with a distance of 10 mm between the two points. A force may then be applied to the center of the two points and the distance of deflection at various amounts of force may be measured. The amount of force required to deflect the 10 mm section of the lead 0.5 mm may be used as the measurement of the stiffness of the lead. Typical units to measure force, such as miliNewtons (mN), may be used. The stiffness of a section of a lead that is less than 10 mm may be measured by forming an elongated section of the lead that is greater than 10 mm and contains the same components as the section of the actual lead. The stiffness of the elongated section may then be measured according to the method described above.

In one embodiment, the transition portion may include a plurality of sub-portions having differing stiffnesses. Each sub-portion may have a stiffness that is less than the stiffness of the adjacent sub-portion in the proximal direction. In one embodiment, the transition portion may include two sub-portions. The first sub-portion may be located adjacent the proximal portion and have a stiffness that is less than the proximal portion. The second sub-portion may have a stiffness that is less than the first sub-portion.

Figure 1:
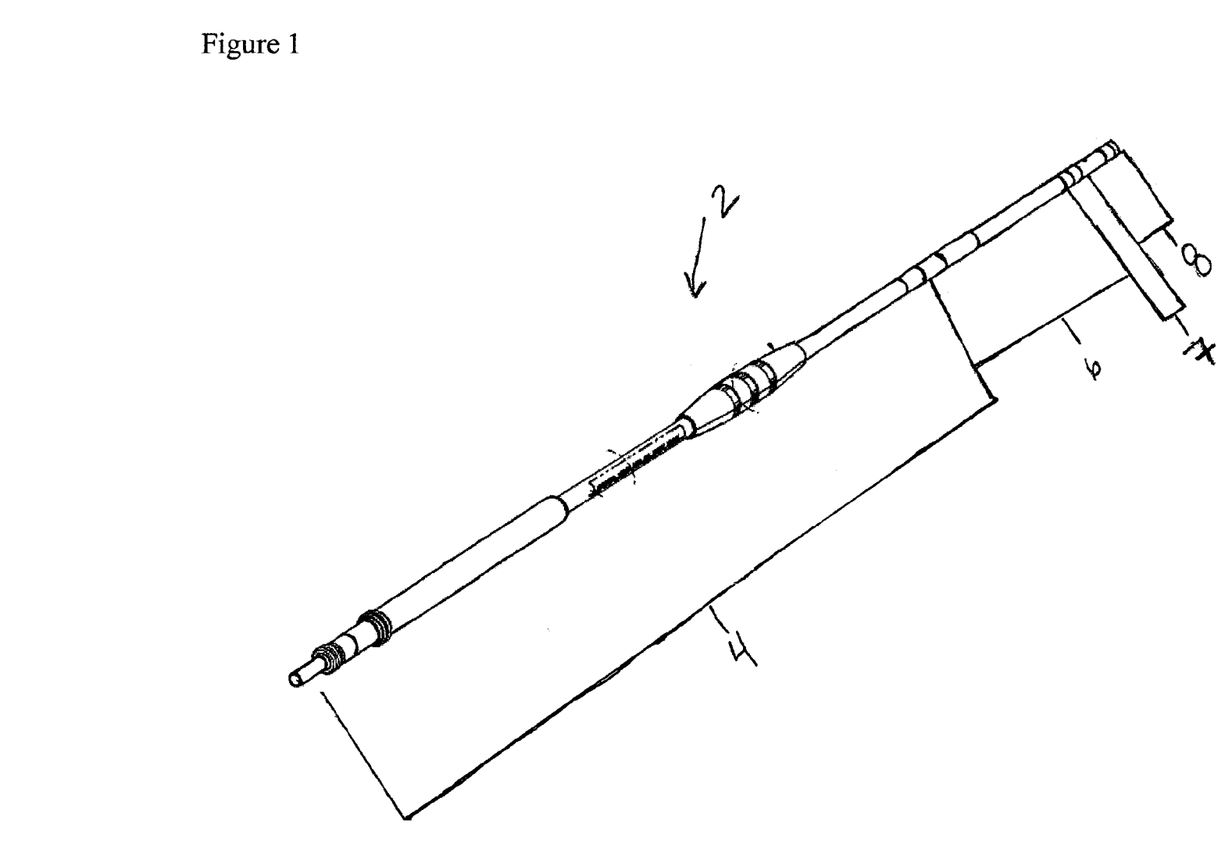
FIG. 1 shows a perspective view of a first embodiment of an implantable medical lead in accordance with the present invention.
Figure 2:
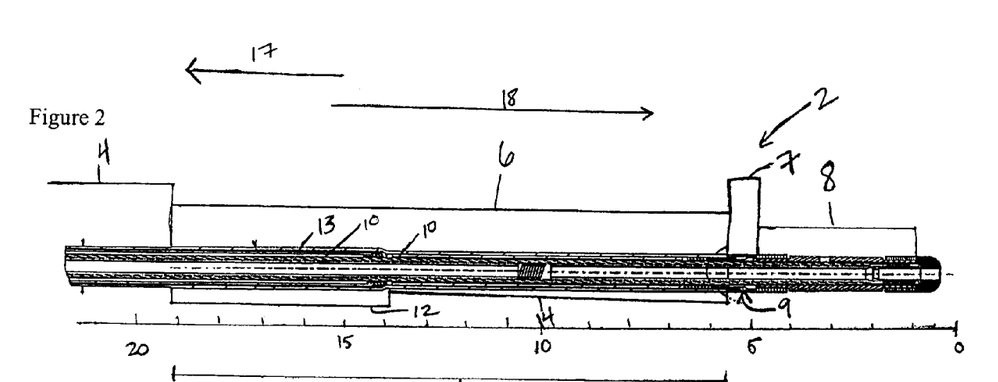
FIG. 2 shows a sectional view of the implantable medical lead of FIG. 1
Figure 3:
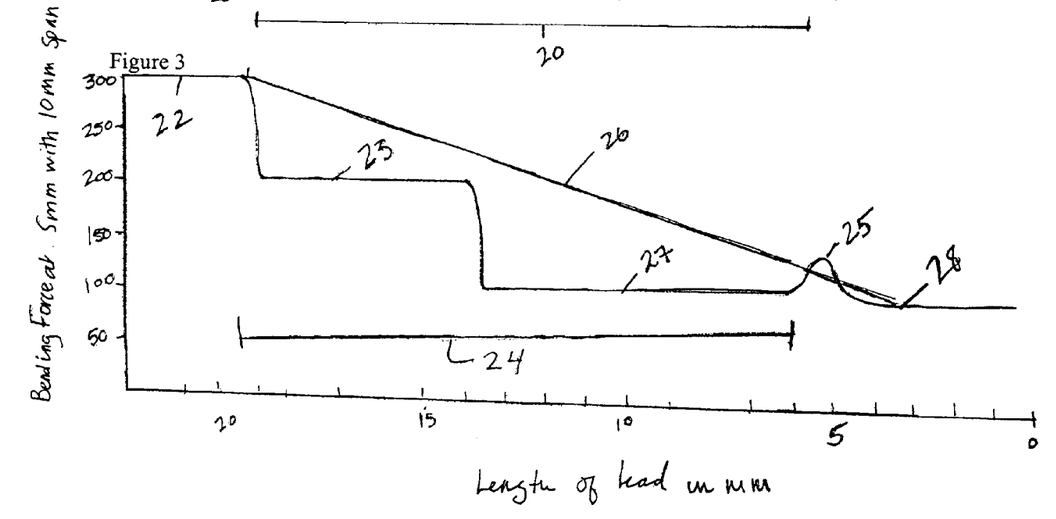
FIG. 3 is a graph showing the stiffness of the implantable medical lead of FIG. 2.

One embodiment is illustrated in FIGS. 1-3. In this embodiment, an elongate implantable medical lead 2 includes a proximal portion 4, a transition portion 6, a mechanical portion 7 which includes a mechanical feature 9, and a distal portion 8. The transition portion 6 has a transition length 20, and includes a first sub-portion 12 and a second sub-portion 14. The transition portion 6 does not include the mechanical portion 7 which has a mechanical stiffness 25 that is greater than the stiffness of the lead in the proximal direction 17. The mechanical feature 9 may include an electrode, sensor, bond portion, observable marker ring such as a fluoromarker ring, extension mechanism, or other features that render the mechanical portion 7 stiffer than the portion of the lead adjacent to the mechanical portion 7 in the proximal direction 17. The first and second sub-portions 12, 14 differ from each other in stiffness and composition. In the illustrated embodiment, the entire transition portion includes polymeric tubing 10. In addition to the polymeric tubing 10, the first sub-portion 12 includes additional polymeric tubing 13 whereas the second sub-portion 14 does not. This additional polymeric tubing 13 results in the first sub-portion 12 becoming more stiff than the second sub-portion 14.

The differences in stiffness in the first sub-portion 12 and second sub-portion 14 can be seen in the graph shown in FIG. 3. The graph plots the stiffness of the lead 2 on the y-axis (labeled "Bending Force at 0.5 mm with 10 mm span") and the length of the lead 2 on the x-axis. In the illustrated embodiment, the proximal portion 4 has a proximal stiffness 22. In one embodiment, the proximal stiffness 22 requires a force of about 310 mN to deflect a 10 mm section of the proximal portion 4 a distance of 0.5 mm in the method described above. The distal portion 8 has a distal stiffness 28 that requires a force of about 75 mN to deflect a 10 mm span of the distal portion 8 a distance of 0.5 mm. The transition portion 6 has a transition stiffness 24. This transition stiffness 24 decreases along the length 20 of the transition portion 6 in the distal direction 18. The transition stiffness 24 includes the stiffness 23 of first sub-portion 12 and the stiffness 27 of the second sub-portion 14. In one embodiment, the first sub-portion stiffness 23 requires about 200 mN to deflect a 10 mm span of the first sub-portion 12 a distance of 0.5 mm out of the plane of the span and the second sub-portion stiffness 27 requires about 90 mN to deflect a 10 mm span of the second sub-portion 14 a distance of 0.5 mm out of the plane of the span. As shown, the mechanical portion 7 has a mechanical stiffness 25 which is greater than the second sub-portion stiffness 27 and therefore is not included in the transition stiffness 24. In other embodiments, the portions 4, 6, 8 may have any stiffness generally known in the art for medical leads so long as the stiffness generally decreases in a distal direction.

The transition stiffness 24 can be measured in relation to a slope 26. The slope 26 represents a linear decrease in stiffness between the proximal stiffness 22 and the distal stiffness 28. The slope 26 is formed by measuring the proximal stiffness 22 and the distal stiffness 28 and plotting the linear decrease between the two. According to the present invention and as illustrated, the transition stiffness 24 does not have to follow the slope 26, or be linear. In the illustrated embodiment, the transition stiffness 24 falls below the slope 26. In some embodiments, the transition stiffness may fall within a certain percentage of the slope, such as within 40% of the slope or 10% of the slope.

FIGS. 4-7 illustrate another embodiment of an implantable medical lead 30. In this embodiment, the lead 30 is formed of electrodes 36, conductors 38, and a polymeric insulator 40 which defines a shaft 41 and insulates the conductors 38. The polymeric insulator 40 may include any suitable materials such as those described above. The lead 30 also includes a proximal portion 32 having a proximal stiffness 58 and a distal portion 54 having a distal stiffness 55, and a transition portion 34 having a transition stiffness 50 between the proximal portion 32 and the distal portion 54. The transition portion 34 in this embodiment is discontinuous and does not include the cross-sectional portions of the lead which include electrodes 36. Therefore, in this embodiment, the transition portion 34 includes a first segment 35 and a second segment 37 which are separated by electrodes 36. In one embodiment, each of the segments 35, 37 may be at least 3 mm in length. In other embodiments, each of the segments may be at least 6 mm in length, or at least 10 mm in length, or more.

Figure 4:
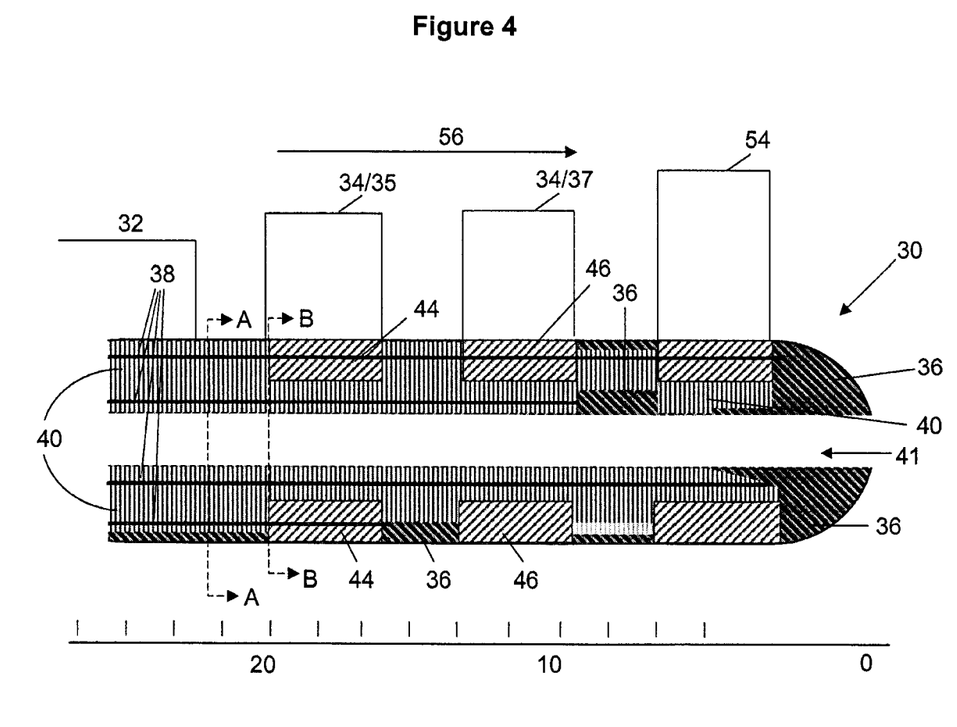
FIG. 4 is a sectional view of a second embodiment of an implantable medical lead in accordance with the present invention.

The first segment 35 has a first segment stiffness while the second segment 37 has a second segment stiffness. The first segment stiffness and the second segment stiffness form the transition stiffness 50. The transition portion may include a first collar 44 in the first segment 35, and a second collar 46 in the second segment 37. The stiffness and size of the collars 44, 46 along with the size and composition of the conductors 38 may be varied to produce a varying transition stiffness 50 that decreases in a distal direction 56. For example, the first collar 44 may be shorter, thicker, and/or formed of stiffer material than the second collar 46. The collars 44, 46 may be formed of any of the suitable polymers described. One or more of the collars 44, 46 may be formed of the same material as the polymeric insulator 40. In other embodiments, the transition portion 34 may include more than two discontinuous segments and/or more than two collars.

Figure 5:
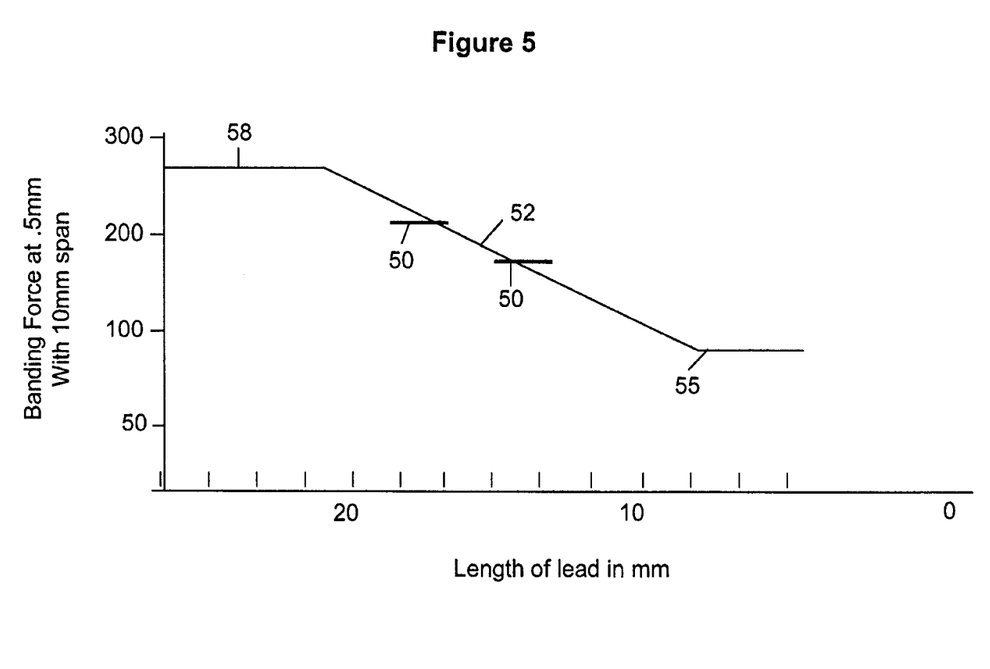
FIG. 5 is a graph showing the stiffness of the implantable medical lead of FIG. 4.

The graph shown in FIG. 5 illustrates the proximal stiffness 58 and the transition stiffness 50. Similar to the graph of FIG. 3, the stiffness of the lead 30, as measured by the method described above, is plotted on the y-axis and the length of the lead 30 is plotted on the x-axis. As shown in FIG. 5, the transition stiffness 50 is discontinuous and does not include the stiffness of the cross-sectional portions of the lead 30 which include electrodes 36. The transition stiffness 50 therefore declines in the distal direction 56. The transition stiffness 50 may also be compared to a slope 52. In this embodiment, the slope 52 is formed by measuring the proximal stiffness 58 with the distal stiffness 55 and plotting the decrease between the proximal stiffness 58 and the distal stiffness 55.

Figure 6:
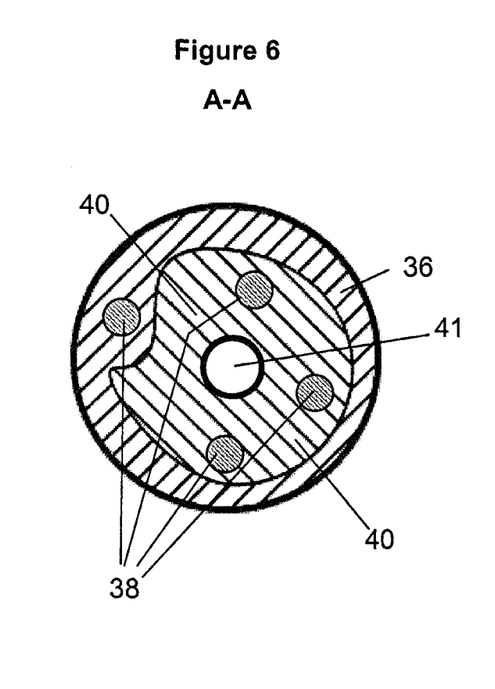
FIG. 6 is a sectional view of the implantable medical lead of FIG. 4 taken along line A-A.

FIG. 6 illustrates a cross-sectional view of the lead at lines A-A on FIG. 4. This portion of the lead includes electrode 36, conductors 38, polymeric insulator 40 surrounding the shaft 41. Since this portion of the lead includes an electrode 36 which increases the stiffness of the lead, this portion is not considered part of the transition portion 34 and therefore the stiffness of this portion is not considered part of the transition stiffness 50.

Figure 7:
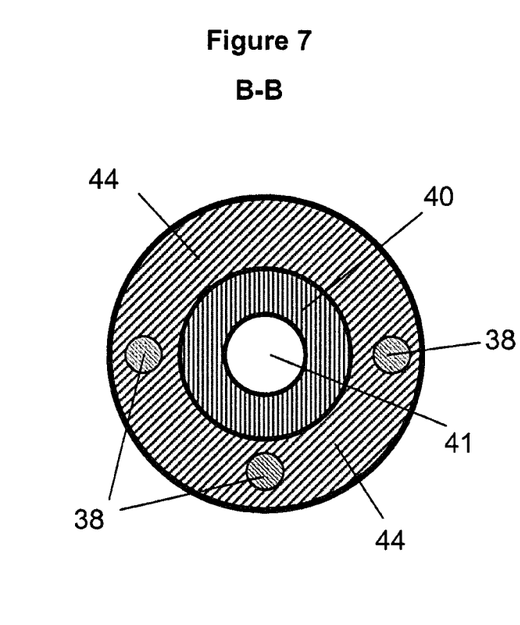
FIG. 7 is a sectional view of the implantable medical lead of FIG. 4 taken along line B-B.

FIG. 7 illustrates a cross-sectional view of the lead at lines B-B on FIG. 4. This portion of the lead includes conductors 38, polymeric insulator 40 surrounding the shaft 41, and the first collar 44. Since this portion of the lead does not includes a mechanical feature which increases the stiffness of the lead, this portion is considered part of the transition portion 34 and therefore the stiffness of this portion is considered part of the transition stiffness 50.

Figure 8:
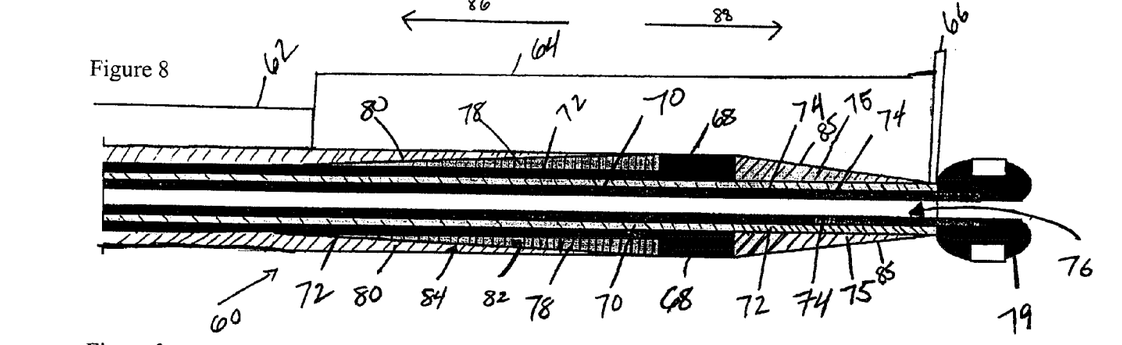
FIG. 8 is a sectional view of a third embodiment of an implantable medical lead in accordance with the present invention.
Figure 9:
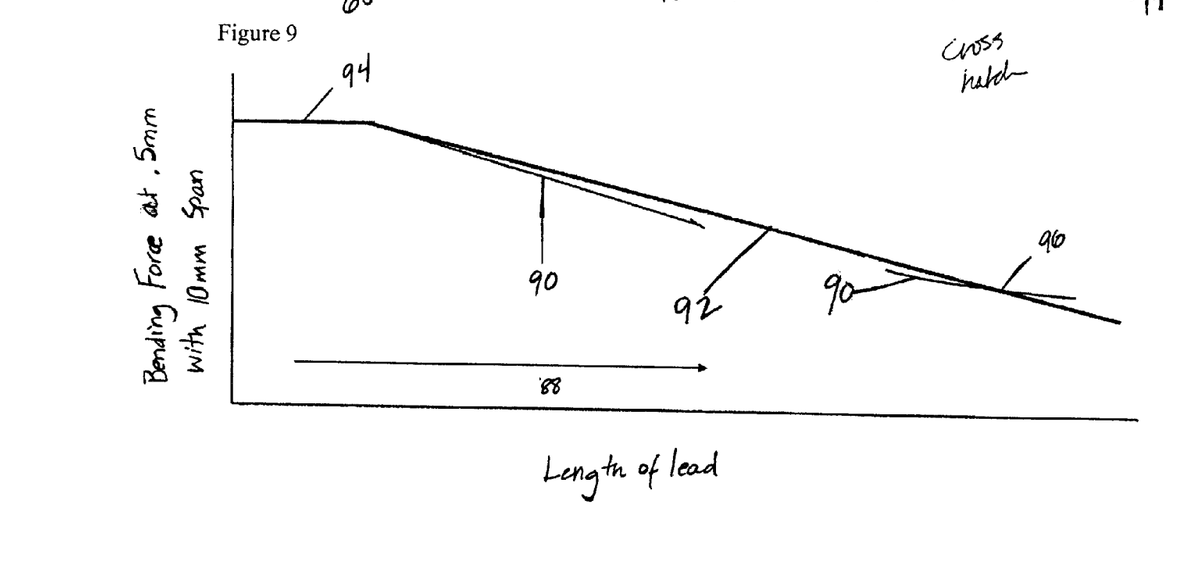
FIG. 9 is a graph showing the stiffness of the implantable medical lead of FIG. 8.

In another embodiment, illustrated in FIGS. 8-9, a medical lead 60 includes a transition portion 64 that includes a first polymeric material 78 having a first stiffness and a first thickness that tapers in a proximal direction 86 and forms a first mating surface 82 and a second polymeric material 80 having a second stiffness that is greater than the first stiffness and a second thickness that tapers in a distal direction 88 and forms a second mating surface 84 that mates with the first mating surface 82. The first and second polymeric materials 78, 80 may include any of the polymeric materials described above. For example, the first polymeric material 78 may be silicone while the second polymeric material 80 may be a polyurethane which has a greater stiffness than silicone. The first polymeric material 78 is disposed onto the outer conductor 72 so that the thickness tapers in a proximal direction 86 and provides a first mating surface 82. The second polymeric material 80 includes a second mating surface 84 that mates with the first mating surface 82 so that the thickness of the second polymeric material 80 tapers in a distal direction 88. In the illustrated embodiment, the taper of the first and second polymeric materials 78, 80 is linear. However, in other embodiments, the taper of the polymeric materials may be parabolic and, as such, impart different rates of decrease in stiffness to the transition portion of the lead.

As the amount of the first polymeric material 78 gradually increases in the distal direction 88 and the amount of the second polymeric material 80 gradually decreases in the distal direction 88, the overall stiffness of the transition portion 64 gradually decreases in the distal direction 88. As the second polymeric material 80 tapers off, the gradual change in stiffness in the transition portion may continue to decrease by forming a third tapering surface 85 that tapers in the distal direction 88. This third tapering surface 85 may be formed of a third polymeric material 75 and may extend to the distal portion 66 to create a continuously gradually decreasing stiffness along the length of the transition portion 64. The third polymeric material 75 may include the same or a different polymer as the first polymeric material 78.

The lead 60 also includes a proximal portion 62 having a proximal stiffness 94 and a distal portion 66 having a distal stiffness 96, an inner conductor 74 which defines a lumen 76 and connects to a distal electrode 79, an outer conductor 72 which connects to a proximal electrode 68, and a polymeric insulator 70 which couples the inner conductor 74 to the outer conductor 72 and the electrode 68.

A graph showing the change in stiffness over the length of the transition portion 64 can be seen in FIG. 9. The transition stiffness 90 generally decreases in the distal direction 88 as the thickness of the less stiff and more flexible first polymeric material 78 increases in the distal direction 88. As described above, a slope 92 is formed by measuring the proximal stiffness 94 with the distal stiffness 96 and plotting the decrease between the two. The transition stiffness 90 can be measured in comparison to the slope 92. In this embodiment, the transition stiffness 90 may be within 10% of the slope.

Figure 10:
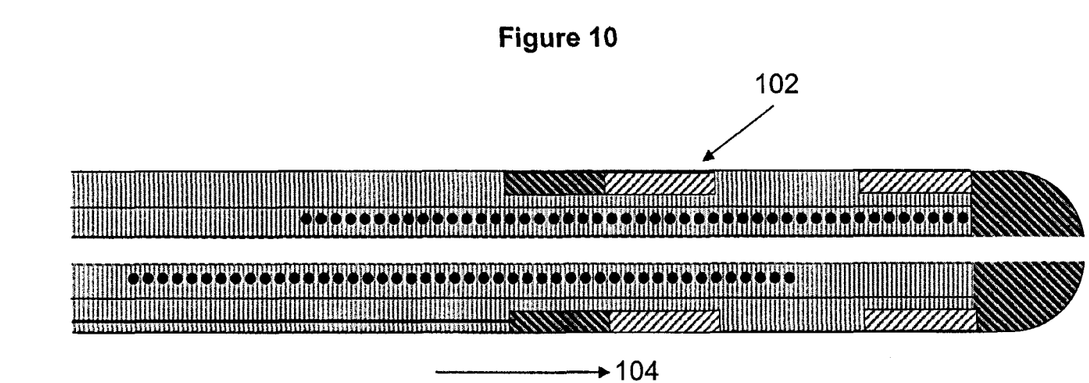
FIG. 10 is a sectional view of a fourth embodiment of an implantable medical lead in accordance with the present invention.
Figure 11:
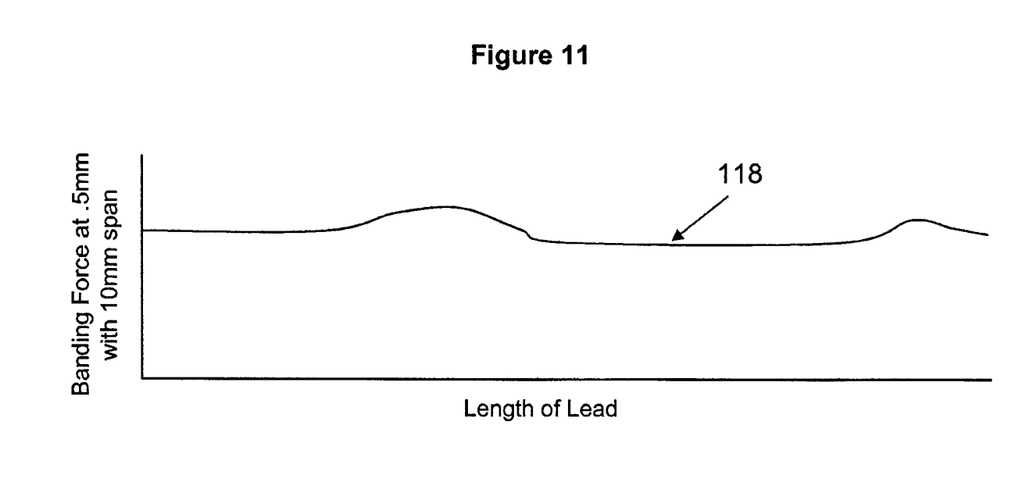
FIG. 11 is a graph showing the stiffness of the implantable lead of FIG. 10.
Figure 12:
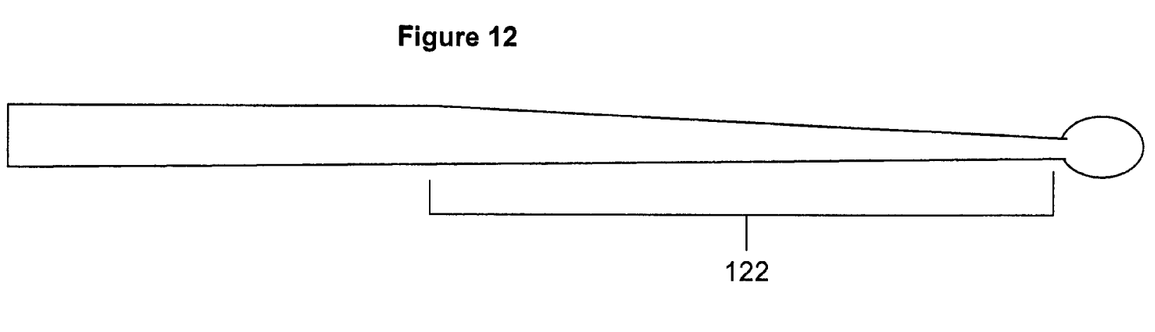
FIG. 12 is a side view of a stylet used in accordance with the present invention.
Figure 13:
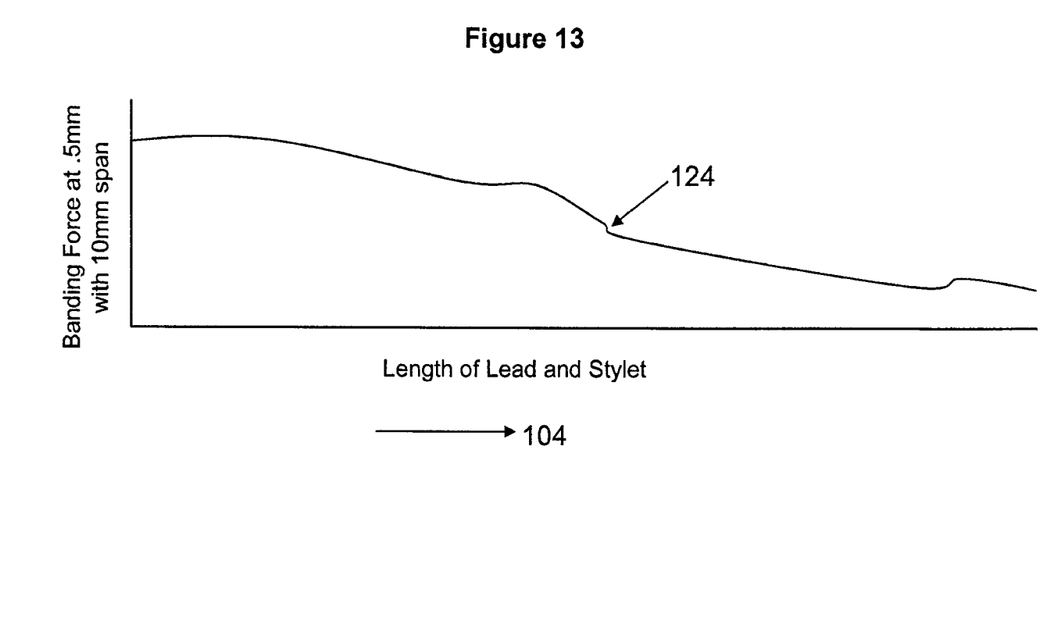
FIG. 13 is a graph showing the composite stiffness of the implantable medical lead of FIG. 10 and the stylet of FIG. 12.

In some embodiments, the combination of a lead and other components, such as a stylet, may provide the variable stiffness in the transition area. For example, FIGS. 10-11 illustrate a lead 102 which does not include a transition portion with a stiffness that decreases. Instead, the lead 102 has a lead stiffness 118 that is relatively constant, as shown in the graph of FIG. 11. This lead 102 may be coupled with a stylet, illustrated in FIG. 12, which has variable stiffness due to a tapering section 122. When the stylet is coupled to the lead 102, the combination of the transition stiffness 118 and the stylet stiffness produce a composite stiffness 124 which generally decreases in a distal direction 104, as illustrated in the graph of FIG. 13.

In another embodiment, a stylet with a may be coupled to a lead that contains a transition portion, such as the lead 60 illustrated in FIG. 8. In this embodiment the stylet may be used, for example, to form a composite stiffness that more closely follows a slope between a proximal stiffness and a distal stiffness than the lead 60 alone.

The transition portion may be any suitable length, such as between about 1-100 mm. The transition portion may be located in any suitable location in relation to the distal tip of the lead. In one embodiment, a distal end of the transition portion may be located between about 5-150 mm of the distal tip of the lead. In another embodiment, the distal end of the transition portion may be located between about 10-40 mm of the distal tip of the lead.

Figure 14:
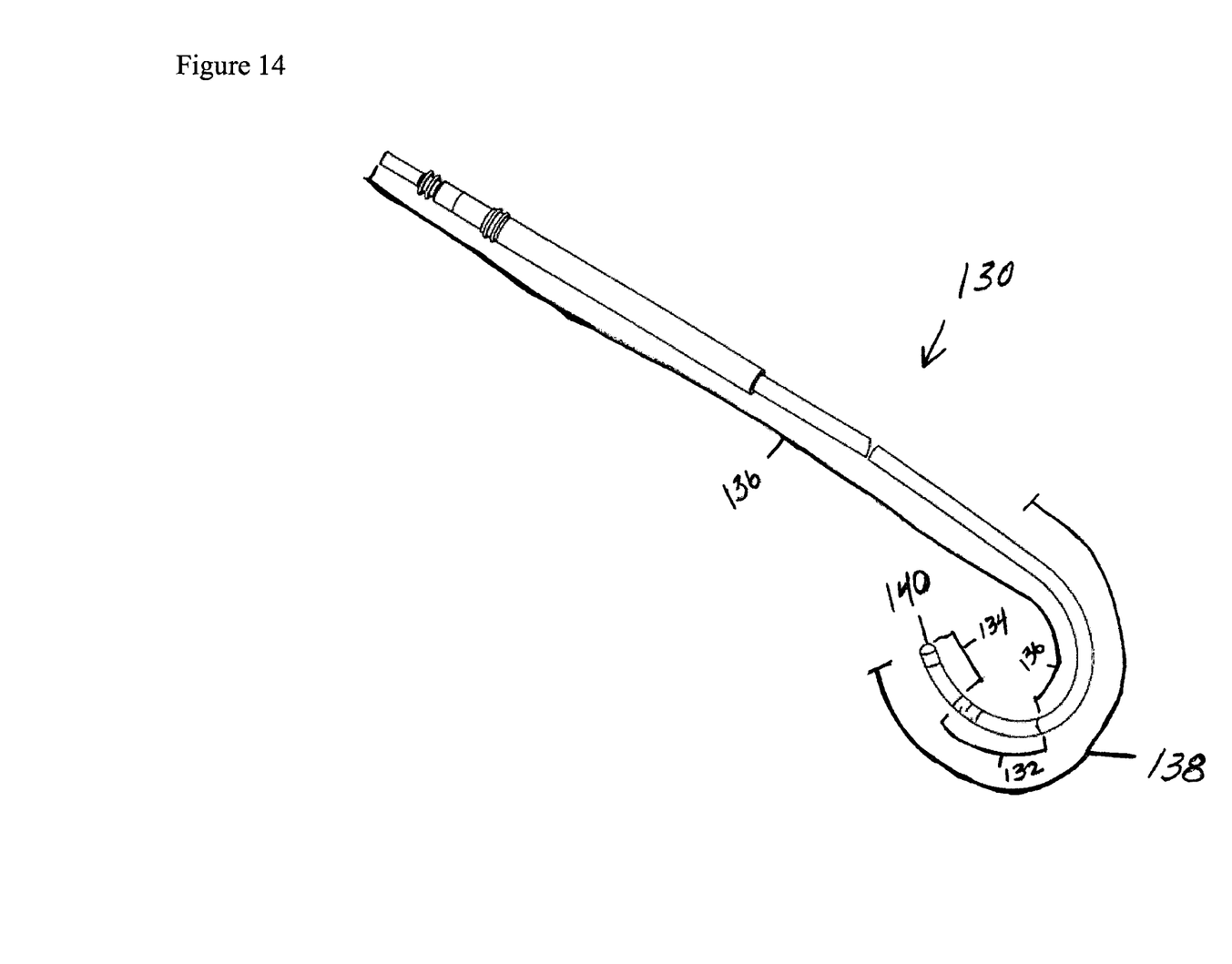
FIG. 14 is a side view of the medical lead of FIG. 1 with a pre-shaped section.

In one embodiment, illustrated in FIG. 14, a medical lead 130 includes a proximal portion 136, a transition portion 132, a distal portion 134, a distal tip 140, and a pre-shaped section 138 located toward the distal tip 140. In this embodiment, at least a portion of the transition portion 132 may be located on the pre-shaped section 138. With this arrangement, the relatively stiffer proximal portion 136 extends further toward the distal tip 140 of the lead and provides more tortional stiffness to the lead. This allows the user to steer the lead, push the distal tip into vessels, and navigate tortuous vessel anatomies more easily. As illustrated, the pre-shaped section 138 may be J-shaped, however it may also be S-shaped, spiral shaped, cant shaped, or any other suitable shapes typically used in leads. Cant shaped leads include multiple bent sections separated by straight sections.

Methods of making a medical lead according to the present invention may depend upon how the variable stiffness along the length of the transition portion is accomplished. For example, if tubes of different polymeric materials are used to create the variable stiffness, then the tubes may be assembled according to their specific stiffness. Furthermore, the conductors and electrodes may be arranged to provide varying stiffness to the transition portion.

In one method, an elongate implantable medical lead illustrated in FIG. 8 is manufactured. This lead may be manufactured by forming a first mating surface 82 that tapers in a proximal direction 86 with a first polymeric material 78 having a first stiffness on the outer conductor 72. A second mating surface 84 may then be formed with a second polymeric material 80 having a second stiffness that is greater that the first stiffness. The second mating surface 84 mates with the first mating surface 82 so that the second mating surface 84 tapers in a distal direction 88. The mating surfaces may be formed by any suitable methods such as molding or dip-coating.

In some embodiments, a first mating surface 82 is formed by molding a first polymeric material 78 to include a first mating surface 82. Conventional methods of molding polymeric materials are suitable for use in this step. Suitable molds may have a ramp section that angles in relation to the shaft 41. When the first polymeric material 78 is then placed in the mold, it forms a tapered surface in relation to the outer conductor 72. In one embodiment, the second mating surface 84 may then be formed with the second polymeric material 80 by dip-coating the first mating surface 82 in the second polymeric material 80. The second polymeric material 80 may then be cured via any curing methods that are suitable for the polymer used. The first polymeric material 78 may be fastened to the outer conductor 72 either before or after the first and second mating surfaces 82, 84 are mated together.

In another embodiment, the first and second polymeric materials 78, 80 are both molded to form the first and second mating surfaces 82, 84. The first and second mating surfaces 82, 84 may then be mated together through any suitable method such as adhesion. In one embodiment, an adhesive may be applied to the first or second mating surfaces 82, 84 to mate the surfaces together. In one embodiment, the first and second polymeric materials 78, 80 are fastened to a sub-assembly of a lead after they are mated together. The sub-assembly of the lead may include, for example, the inner conductor 74, the polymeric insulator 70, and the outer conductor 72. In another embodiment, the first polymeric material 78 is fastened to the sub-assembly of the lead 60 before the second polymeric material 80 is mated to the first polymeric material 78 via the mating surfaces 82, 84.

In another embodiment, not shown, the second mating surface is formed before the step of forming the first mating surface. The second, stiffer, polymeric material may be molded or dip-coated onto an outer surface of a shaft coating so that the second mating surface tapers in the proximal direction. The first, less stiff, polymeric material may then be molded or dip-coated onto the second mating surface so that the second polymeric material tapers in a proximal direction.

As stated above, many biocompatible polymeric materials are known and can be used to form the medical leads of the present invention. In one embodiment, however, the first polymeric material may include silicone and the second polymeric material may include polyurethane.

Depending on the polymeric materials used to form the lead body, additional steps may optionally be done to further harden the polymeric materials. For example, various annealing processes or crosslinking processes may be performed on the first or second polymeric materials, if desired, to achieve the desired stiffness in the proximal, transition, and distal portions.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An elongate lead comprising:
a lead body having a pre-shaped section biased to a J-shaped configuration, the lead body including a proximal portion, a distal portion and a transition portion disposed between the proximal portion and the distal portion, the lead body having a first step reduction in stiffness between the proximal portion and the transition portion as a result of the proximal portion including polyurethane and the transition portion including silicone, the transition portion including a first sub portion and a second sub portion, the transition portion and the distal portion defining at least part of the pre-shaped section such that the transition portion and the distal portion are biased to the J-shaped configuration;
an inner polymeric layer defining a lumen extending through the lead body;
an additional polymeric tubing extending over the first sub portion of the transition portion such that the first sub portion is more stiff than the second sub portion, the lead body having a second step reduction in stiffness as a result of the additional polymeric tubing terminating at a transition point between the first sub portion and the second sub portion; and
an electrode disposed between the transition portion and the distal portion, the electrode disposed within the pre-shaped section that is biased to the J-shaped configuration.

2. The elongate lead of claim 1, wherein the proximal portion has a stiffness such that a force required for a deflection of 0.5 mm over a 10 mm span is about 310 mN.

3. The elongate lead of claim 1, wherein the distal portion has a stiffness such that a force required for a deflection of 0.5 mm over a 10 mm span is about 75 mN.

4. The elongate lead of claim 1, wherein the first sub portion of the transition region has a stiffness such that a force required for a deflection of 0.5 mm over a 10 mm span is about 200 mN and the second sub portion of the transition region has a stiffness such that a force required for a deflection of 0.5 mm over a 10 mm span is about 90 mN.

5. An elongate lead comprising:
a lead body including a proximal portion, a distal portion and a transition portion disposed between the proximal portion and the distal portion, the transition portion including a first sub portion and a second sub portion;
the proximal portion having a stiffness such that a force required for a deflection of 0.5 mm over a 10 mm span is about 310 mN;

the distal portion having a stiffness such that a force required for a deflection of 0.5 mm over a 10 mm span is about 75 mN;

the first sub portion of the transition region having a stiffness such that a force required for a deflection of 0.5 mm over a 10 mm span is about 200 mN; and the second sub portion of the transition region having a stiffness such that a force required for a deflection of 0.5 mm over a 10 mm span is about 90 mN.

6. The elongate lead of claim 5, wherein the lead body has a first step reduction in stiffness between the proximal portion and the transition portion as a result of the proximal portion including polyurethane and the transition portion including silicone.

7. The elongate lead of claim 5, wherein the lead body includes an inner polymeric layer defining a lumen extending through the lead body, and the lead body further comprises an additional polymeric tubing extending over the first sub portion of the transition portion such that the first sub portion is more stiff than the second sub portion, the lead body having a second step reduction in stiffness as a result of the additional polymeric tubing terminating at a transition point between the first sub portion and the second sub portion.

8. The elongate lead of claim 5, wherein the transition portion and the distal portion define at least part of a pre-shaped section that is biased to a J-shaped configuration.

* * * * *